United States Patent [19]

Su et al.

[11] Patent Number: 5,601,830
[45] Date of Patent: Feb. 11, 1997

[54] *STAPHYLOCOCCUS AUREUS* ENTEROTOXIN H AND METHODS OF USE

[75] Inventors: Yi C. Su; Amy C. Lee Wong, both of Madison, Wis.

[73] Assignee: Wisconsin Alumni Research Foundation, Madison, Wis.

[21] Appl. No.: 414,804

[22] Filed: Mar. 31, 1995

[51] Int. Cl.[6] .......................... A61K 39/085; C07K 1/00; C07K 2/00

[52] U.S. Cl. ........................ 424/237.1; 530/300; 530/350

[58] Field of Search ........................... 435/7.32; 530/300, 530/350, 825; 424/237.1

[56] References Cited

U.S. PATENT DOCUMENTS 5,302,388 4/1994 Doyle et al. .

OTHER PUBLICATIONS

Ren, Keyong, Jason D. Bannan, Vijajkumar Pancholi, Ambrose L. Cheung, John C. Robbins, Vincent A. Fischetti, and John B. Zabriskie 1994. Characterization and Biological Properties of a New Staphylococcal Exotoxin. J. Exp. Med. 180: 1675–1683.

Avena, R. M. and M. S. Bergdoll. 1967. Purification and some physicochemical properties of enterotoxin C, *Staphylococcus aureus strain* 361. Biochemistry. 6:1474–1480.

Bergdoll, M. S., M. J. Surgalla, and G. M. Dack. 1959. Staphylococcal enterotoxin: identification of a specific precipitating antibody with enterotoxin neutralizing property. J. Immunol. 83:334–338.

Bergdoll, M. S., C. R. Borja, and R. M. Avena. 1965. Identification of a new enterotoxin as enterotoxin C. J. Bacteriol. 90:1481–1485.

Bergdoll, M. S., C. R. Borja, R. N. Robbins, and K. F. Weiss. 1971. Identification of enterotoxin E. Infect. Immun. 4:593–595.

Bergdoll, M. S., 1983. Enterotoxins, pp. 559–598. In C. Adlam and C. S. F. Easmon (ed.), Staphylococci and Staphylococcal Infections, vol. 2, Academic Press, Inc., London.

Bergdoll, M. S. 1989. *Staphylococcus aureus,* pp. 463–523. In M. P. Doyle (ed.), Foodborne Bacterial Pathogens. Marcel Dekker, Inc., New York.

Betley, M. J., D. W. Borst, and L. B. Regassa. 1992. Staphylococcal enterotoxins, toxic shock syndrome toxin and streptococcal pyrogenic exotoxins: a comparative study of their molecular biology. Chem. Immunol. 55:1–35.

Casman, E. P. 1960. Further serological studies of staphylococcal enterotoxin. J. Bacteriol. 79:849–856.

Casman, E. P., R. W. Bennett, A. E. Dorsey, and J. A. Issa. 1967. Identification of a fourth staphylococcal enterotoxin, enterotoxin D. J. Bacteriol. 94:1875–1882.

Fazekus et al., 1980. J. Immunol. Methods, 35:1.

Freed, R. C., M. L. Evenson, R. F. Reiser, and M. S. Bergdoll. 1982. Enzyme–linked immunosorbent assay for detection of staphylococcal enterotoxins in food. Appl. Environ. Microbiol. 44:1349–1355.

Kokan, N. P. and M. S. Bergdoll. 1987. Detection of low–enterotoxin–producing *Staphylococcus aureus* strains. Appl. Environ. Microbiol. 53:2675–2676.

Laemmli, U. K. 1970. Cleavage of structural proteins during the assembly of the head of bacteriophage T4. Nature. 227:680–685.

Munson, S. H. and M. J. Betley. 1991. Partial characterization of a new staphylococcal enterotoxin gene, abstr. B–36, p. 31. Abstr. 91th Annu. Meet. Am. Soc. Microbiol. 1991.

Reiser, R. F., R. N. Robbins, G. P. Khoe, and M. S. Bergdoll. 1983. Purification and some physicochemical properties of toxic–shock toxin. Biochem. 22:3907–3912.

Reiser, R. F., R. N. Robbins, A. L. Noleto, G. P. Khoe, and M. S. Bergdoll, 1984. Identification, purification, and some physicochemical properties of staphylococcal enterotoxin $C_3$. Infect. Immun. 45:625–630.

Robbins, R. N., and M. S. Bergdoll. 1984. Production of rabbit antisera to the staphylococcal enterotoxins. J. Food Prot. 47:172–176.

Robbins, R., S. Gould,and M. Bergdoll. 1974. Detecting the enterotoxigenicity of *Staphylococcus aureus* 1strains. Appl. Microbiol. 28:946–950.

Saunders, G. C. 1979. The art of solid enzyme immunoassay including selected protocols, pp. 98–119. In R. M. Nakamura, R. W. Dito, and E. S. Tucker (ed.), Immunoassays in the clinical laboratory. Alan R. Liss, Inc., New York.

Saunders, G. C., and M. L. Bartlett. 1977. Double–antibody solid–phase enzyme immunoassay for the detection of staphylococcal enterotoxin A. Appl. Environ. Microbial. 34:518–522.

Su, Y.–C. and A. C. L. Wong. 1993. Optimal condition for the production of unidentified staphylococcal enterotoxins. J. Food Prot. 56:313–316.

Surgalla, M. J., M. S. Bergdoll, and G. M. Dack. 1953. Some observations on the assay of staphylococcal enterotoxin by the monkey–feeding test. J. Lab. Clin. Med. 41:782–788.

Todd, E. C. D. 1989. Preliminary estimates of costs of foodborne disease in the United States. 1989 J. Food Prot. 52:595–601.

*Primary Examiner*—James C. Housel
*Assistant Examiner*—Jennifer Shaver
*Attorney, Agent, or Firm*—DeWitt Ross & Stevens SC

[57] ABSTRACT

The isolation and characterization of a novel staphylococcal enterotoxin designated SEH is described. A process for high-yield generation of substantially pure SEH and antibodies specific thereto is described, as is construction of an immunoassay for detection and quantification of SEH within a sample.

10 Claims, 7 Drawing Sheets

STAPHYLOCOCCUS AUREUS ENTEROTOXIN H AND METHODS OF USE

This invention was made with United States Government support awarded by USDA, project No. 3294. The United States Government has certain rights in this invention.

FIELD OF THE INVENTION

The present invention is directed to the identification, isolation, and characterization of novel staphylococcal enterotoxins (SE's) from *Staphylococcus aureus* and other staphylococci species, and antibodies thereto. The invention is also drawn to methods of using the SE's and antibodies.

REFERENCE TO CITATIONS

Full bibliographic citations to the references cited in this application can be found in the Bibliography section preceding the claims.

DESCRIPTION OF THE PRIOR ART

Staphylococcal enterotoxins (SE's), are a class of extracellular proteins produced by many strains of the *Staphylococcus aureus* bacteria as well as other staphylococci species. SE's were first identified in 1959, (Bergdoll et al., 1959), and seven serologically distinct SE's have now been identified. For clarity and brevity, the various SE's are identified hereinbelow by the alphabetic designation "SE," followed by an alphanumeric designation for each distinct enterotoxin. The seven presently known SE's are designated as follows: SEA (Casman, 1960), SEB (Bergdoll et al., 1959), $SEC_1$ (Bergdoll et al., 1965), $SEC_2$ (Avena et al, 1967), $SEC_3$ (Reiser et al, 1984), SED (Casman et al, 1967), and SEE (Bergdoll et al., 1971) The unmodified designation "SE" shall be used hereinbelow to refer to staphylococcal enterotoxins as a generic class of extracellular compounds secreted by many strains of staphylococci.

SE's are medically and economically significant because they are the causative agents of staphylococcal food-borne poisoning. Staphylococcal food poisoning results in bouts of violent emesis, as well as other gastrointestinal symptoms. In the United States alone, the costs incurred by both food producers and consumers due to staphylococcal food poisoning has been estimated to be approximately $1.5 billion annually (Todd, 1989).

Of primary concern to the public health is the fact that epidemiological studies of staphylococcal food poisoning outbreaks indicate that approximately 5% of these outbreaks are caused by unidentified SE's which are serologically distinct from the seven known SE's listed above (Bergdoll, 1983). While accurate assays for the seven known SE's are available, the medical and economic difficulties caused by the unidentified SE's are greatly exacerbated because there is currently no easy means for detecting the presence of unidentified SE's.

The only known assay for determining the presence of an unidentified SE is a monkey feeding assay (Surgalla et al., 1953). A crude and expensive assay, the method entails feeding a suspected food source or culture supernatant from growth of a suspect staphylococcal strain to rhesus monkeys, and observing the monkeys for emesis. The presence of unidentified SE's will normally induce vomiting in the monkeys within 6 hours after ingestion of the tainted food or culture supernatant.

The monkey feeding assay is extremely expensive, labor intensive, slow, incapable of distinguishing between serologically different SE's (or between any other emetic agents), and wholly impractical for routine screening for unidentified SE's in food products. Due to the lack of an economically-acceptable assay, food industries are unable to monitor their products for the presence of the as yet unidentified SE's.

Clearly then, there is a need for a simple, reliable, rapid, sensitive, and inexpensive method for detecting the presence of unidentified SE's in a food source or other sample.

The most recently characterized of the known SE's, $SEC_3$, was isolated in 1984 by Reiser and co-workers. However, Betley and co-workers have examined DNA from *S. aureus* strains that produced uncharacterized SE's, and identified a new enterotoxin gene designated seg+(Betley et al., 1992). The gene was identified by hybridization of the seg+-containing DNA of *S. aureus* strain MJB801 to an sec+-containing probe. Analysis of the recombinant clones indicated that an emetic toxin, designated SEG, is encoded by the seg+gene. While the seg+gene has been partially sequenced (Munson and Betley., 1991), the SEG protein itself has not been isolated or characterized.

SUMMARY OF THE INVENTION

The present invention is directed to a substantially pure protein composition isolatable from *Staphylococcus aureus* and other species of staphylococci, having an N-terminal amino acid sequence of Glu Asp Leu His Asp Lys Ser Glu Leu Thr Asp Leu Ala Leu Ala Asn Ala Tyr Gly Gln Tyr Asn His Pro Phe Ile Lys Glu Asn Ile, and having the following physical properties:

| | |
|---|---|
| Isoelectric point | 5.7 |
| Molecular weight | 28.5 kD (SDS-PAGE) |
| | 27.3 kD (Sephacryl gel filtration). |

The present invention is also directed to a substantially pure staphylococcal enterotoxin designated SEH having an N-terminal amino acid sequence of Glu Asp Leu His Asp Lys Ser Glu Leu Thr Asp Leu Ala Leu Ala Asn Ala Tyr Gly Gln Tyr Asn His Pro Phe Ile Lys Glu Asn Ile, and having the following physical properties:

| | |
|---|---|
| Isoelectric point | 5.7 |
| Molecular weight | 28.5 kD (SDS-PAGE) |
| | 27.3 kD (Sephacryl gel filtration). |

The present invention is further directed to a bioreagent suitable for antibody assays comprising a substantially pure protein composition or staphylococcal enterotoxin having the properties described immediately above.

Further still, the invention is directed to polyclonal and monoclonal antibodies specific to staphylococcal enterotoxin designated SEH.

The invention is also directed to a diagnostic kit for assaying the presence of SEH in a sample. The diagnostic kit includes the polyclonal or monoclonal antibodies described above disposed in at least one container, and directions for its use.

The invention also describes an immunoassay method for the detection of SEH which includes the steps of contacting a sample to be tested for the presence of SEH with an antibody specific to SEH, thereby forming an immune complex, and determining the presence of the immune complex to thereby determine the presence of SEH in the sample.

Further, the present invention is directed to a process for isolating and purifying staphylococcal enterotoxins from cells, including the steps of:

cultivating staphylococci cells in a medium containing the nutritional substances necessary to support the growth and multiplication of the cells;

separating the medium from the cells;

isolating proteinaceous materials from the medium to yield a crude protein mixture; and isolating substantially pure staphylococcal enterotoxins from the crude protein mixture.

The method can be further optimized by cultivating the staphylococci cells in a medium specifically designed to maximize the cellular production of enterotoxins.

This high-yield purification method allows qualitative and quantitative identification of a previously unknown enterotoxin, which has been designated SEH. The method of the present invention allows for the quantitative determination of the activity, molecular weight, isoelectric point, and N-terminal amino acid sequence of SEH, along with other physical and serological data.

Figure 1:
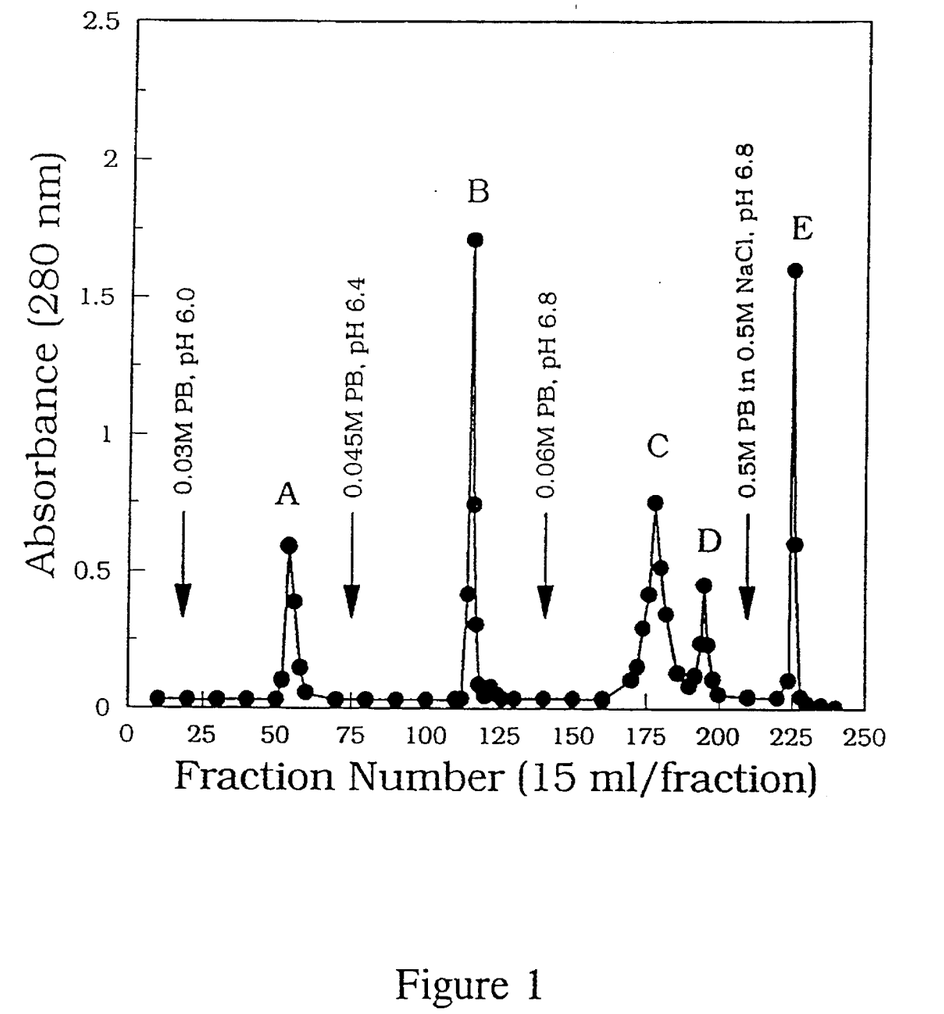
FIG. 1 is an elution profile of CM-Sepharose FL ion-exchange chromatography for the crude material isolated from culture supernate by batch adsorption chromatography. Concentrated eluate from CG-50 batch adsorption was applied to a column containing 150 mL of CM-Sepharose FL, and eluted by step-wise addition of phosphate buffered solutions of increasing pH. SEH eluted in peak A.
Figure 2:
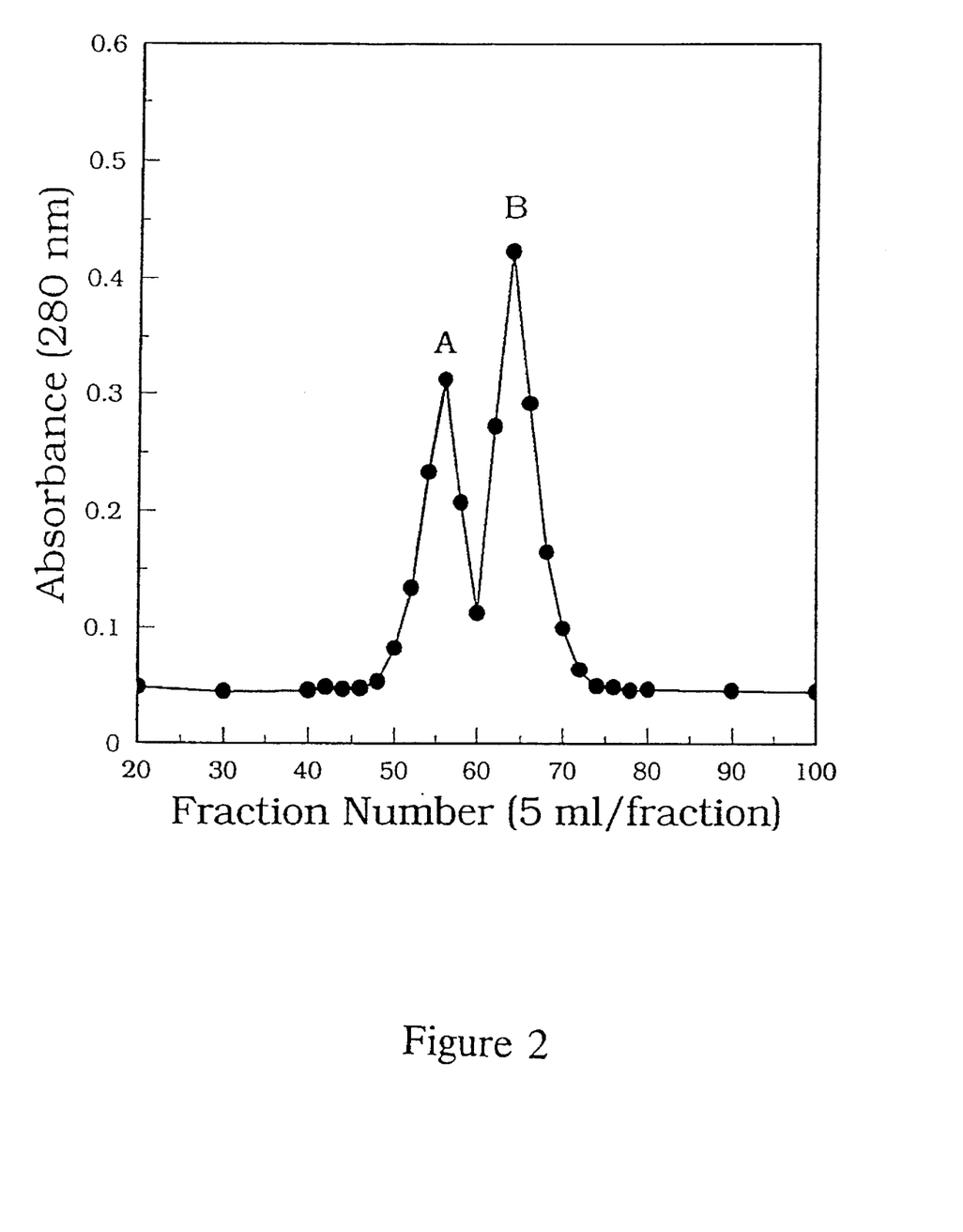
FIG. 2 is an elution profile of Sephacryl 100 HR gel filtration chromatography of concentrated toxin obtained by ion-exchange chromatography. Concentrated toxin from CM-Sepharose FL ion-exchange chromatography was applied to a column containing 500 mL of Sephacryl 100 HR and eluted with 0.05M phosphate buffer containing 0.5M NaCl, pH 6.8. SEH eluted in peak A.
Figure 3:
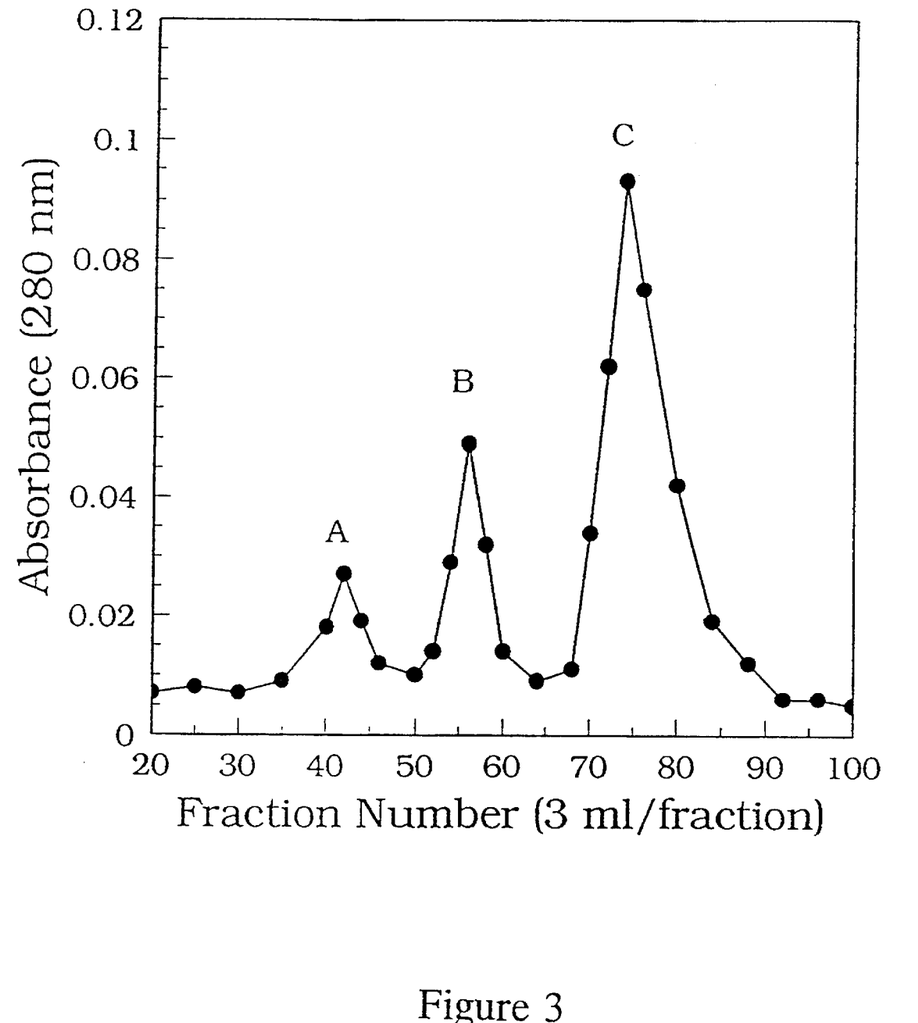
FIG. 3 is an elution profile of Bio-Gel P-30 gel filtration chromatography of concentrated toxin obtained by Sephacryl gel filtration. Lyophilized toxin from Sephacryl gel filtration was applied to a column containing 500 mL of Bio-Gel P-30 gel and eluted with 0.05M phosphate buffer containing 0.5M NaCl, pH 6.8. SEH eluted in peak B.
Figure 4:
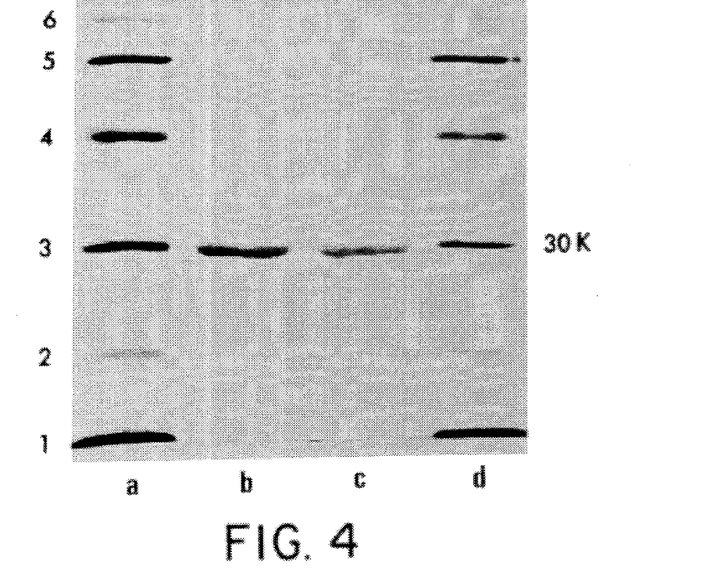
FIG. 4 shows the results of SDS-PAGE of purified SEH. Lanes a and d are molecular-weight-standard proteins: (1) a-lactalbumin (14.4 kD), (2) soybean trypsin inhibitor (20.1 kD), (3) carbonic anhydrase (30.0 kD), (4) ovalbumin (43.3 kD), (5) bovine serum albumin (67.08 kD), and (6) phosphorylase b (94.0 kD). Lane b: Purified SEH without B-mercaptoethanol treatment. Lane c: Purified SEH treated with B-mercaptoethanol.
Figure 5:
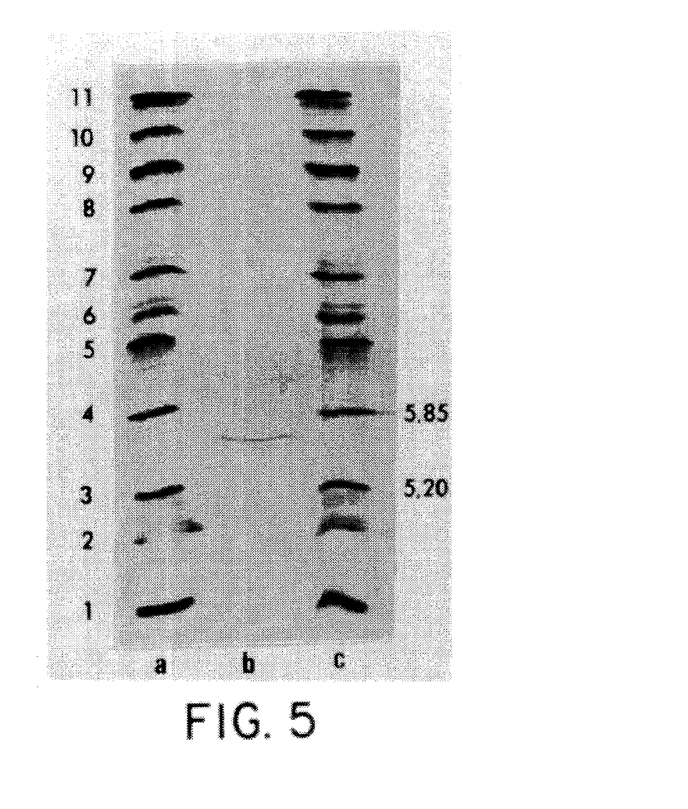
FIG. 5 shows the results of isoelectric focusing of SEH prepared according to the described process. Lanes a and c are pI markers: (1) amyloglucosidase (3.50), (2) soybean trypsin inhibitor (4.55), (3)B-lactoglobulin A (5.20), (4) bovine carbonic anhydrase B (5.85), (5) human carbonic anhydrase B (6.55), (6) horse myoglobin—acidic band (6.85), (7) horse myoglobin—basic band (7.35), (8) lentil lectin—acidic band (8.15), (9) lentil lectin—middle band (8.45), (10) lentil lectin- basic band (8.65), and (11) trypsinogen (9.30). Lane b: Purified SEH.

SEH purified using the above-described process is very pure, yielding only one band on SDS-PAGE under both reducing and non-reducing conditions (See FIG. 4). Similar to previously-identified SE's, SEH appears to be a simple, emetic, and antigenic protein.

The present invention is particularly useful to food industries, regulatory agencies, and analytical laboratories for monitoring and testing food supplies for SE contamination. The present invention also has specific applicability to epidemiological studies, as well as for control and treatment of food poisoning caused by SE's in general, and SEH in particular.

In light of the above discussion, it is a principal object of the present invention to identify previously unknown staphylococcal enterotoxins.

Another object of the invention is to provide a process to quickly and quantitatively isolate SEH.

Yet another object of the present invention is to provide substantially pure SEH.

A further object of the invention is to provide polyclonal and monoclonal antibodies specific to SEH.

A still further object of the invention is to provide a reliable, specific, and commercially cost-effective assay for determining the presence of SEH in a sample.

It is another object of the invention to provide a diagnostic kit for testing a sample for the presence of SEH.

These and other objects and advantages of the invention will become apparent upon a reading of the following "Detailed Description," and attached Drawing FIGS., which set forth the preferred embodiment of the invention.

DETAILED DESCRIPTION OF THE INVENTION

AMINO ACIDS

The following one or three-letter amino acid nomenclature conventions are used throughout the specification and claims:

| Abbreviated Designation | Amino Acid |
| --- | --- |
| A Ala | Alanine |
| C Cys | Cysteine |
| D Asp | Aspartic acid |

-continued

| Abbreviated Designation | Amino Acid |
|---|---|
| E Glu | Glutamic acid |
| F Phe | Phenylalanine |
| G Gly | Glycine |
| H His | Histidine |
| I Ile | Isoleucine |
| K Lys | Lysine |
| L Leu | Leucine |
| M Met | Methionine |
| N Asn | Asparagine |
| P Pro | Proline |
| Q Gln | Glutamine |
| R Arg | Arginine |
| S Ser | Serine |
| T Thr | Threonine |
| V Val | Valine |
| W Trp | Tryptophan |
| Y Tyr | Tyrosine |

STAPHYLOCOCCUS ENTEROTOXIN H (SEH)

Figure 6:
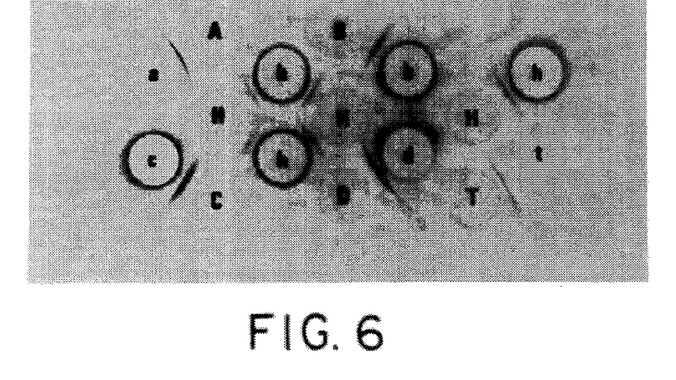
FIG. 6 is an immunodiffusion assay of known SE's, SEH, and toxic shock syndrome toxin 1 (TSST-1): Well A:SEA (8 µg/mL); B:SEB (8 µg/mL); C:SEC (8 µg/mL); D: SED (8 µg/mL); H:SEH (10 µg/mL); T:TSST-1 (10 µ/mL). Well a: anti-SEA serum; b: anti-SEB serum; c: anti-SEC serum; d: anti SED serum; h: anti-SEH serum; t: anti-TSST-1 serum.
Figure 7:
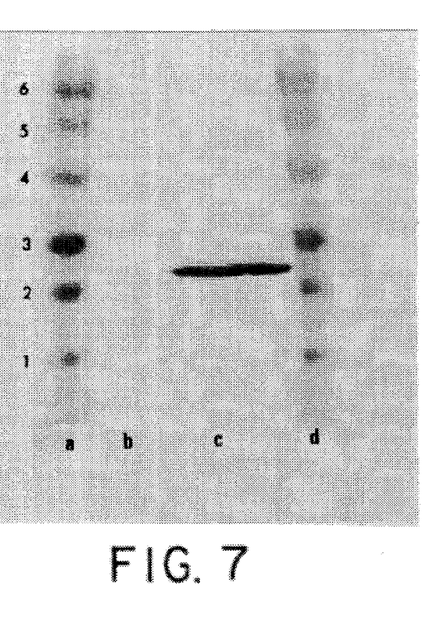
FIG. 7 is a Western blot assay of SEH. Lanes a and d are pre-stained low molecular weight standards: (1) lysozyme (16.0 kD), (2) soybean trypsin inhibitor (24.0 kD), (3) carbonic anhydrase (33.0 kD), (4) ovalbumin (47.0 kD), (5) bovine serum albumin (84.0 kD), (6) phosphorylase B (110.0 kD). Lane b: Concentrated culture supernate (5X) from the growth of S. aureus strain FRI-572. Lane c: Purified SEH.
Figure 8:
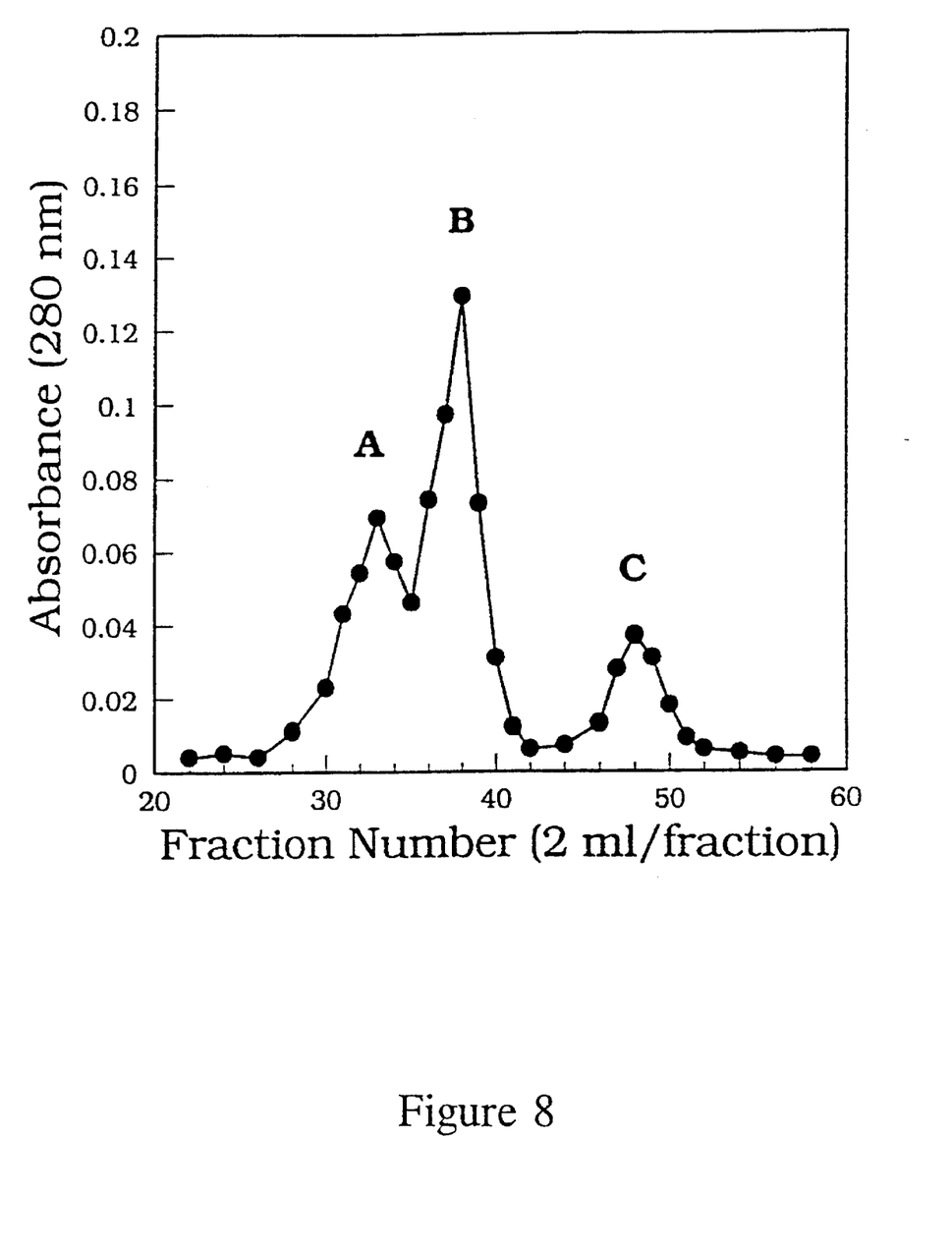
FIG. 8 is an elution profile of antibody-enzyme conjugate solution for ELISA. Antibody-enzyme conjugate solution was applied to a column containing 140 mL of Sephacryl 300 and eluted with 0.05M phosphate buffer containing 0.5M NaCl, pH 6.8. Antibody-enzyme conjugate eluted in peak A, unconjugated antibody in peak B, and peroxidase in peak C.
Figure 9:
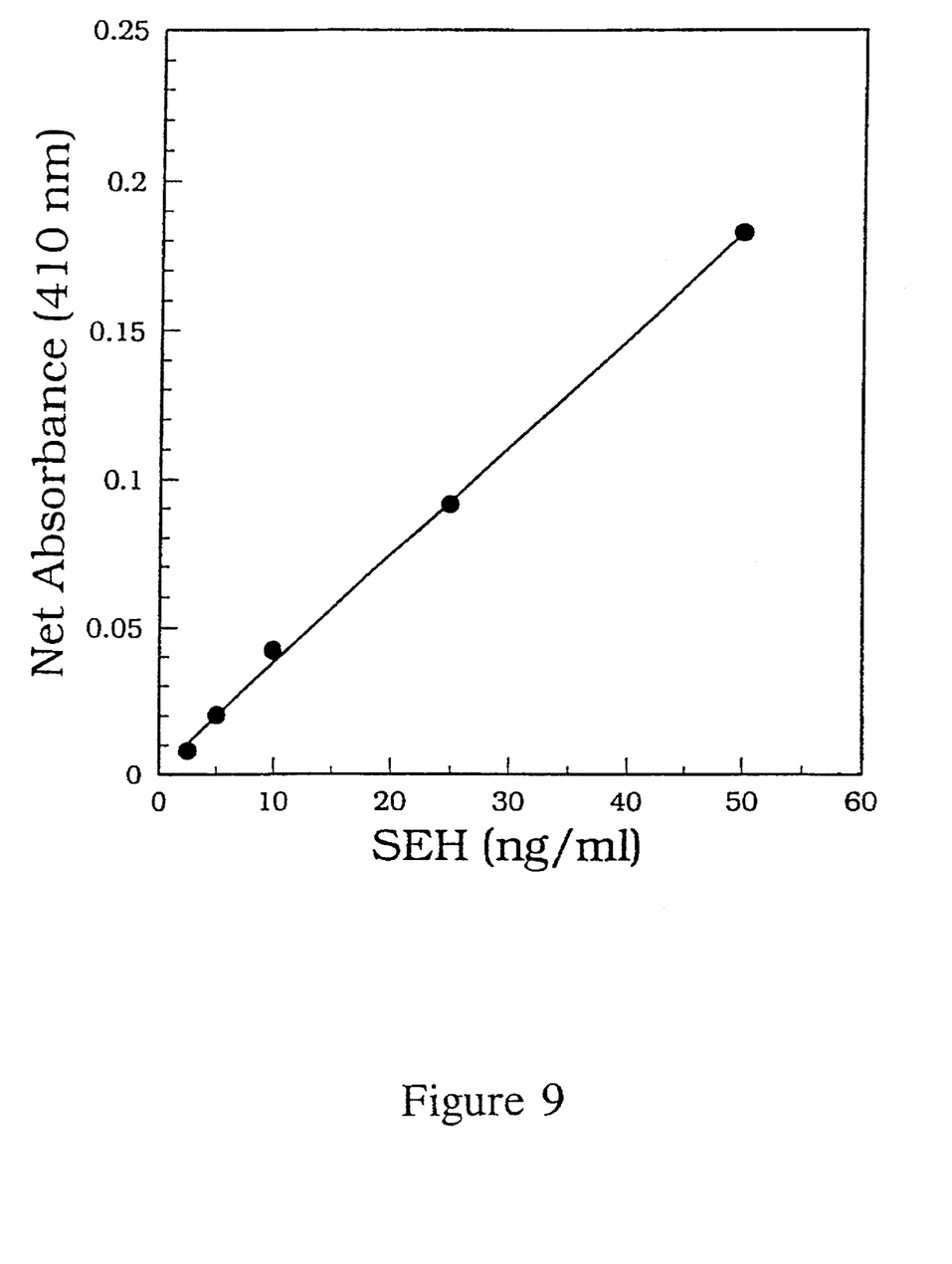
FIG. 9 is a standard curve for determination of SEH by ELISA. The curve is linear between 2.5 and 50 ng/mL SEH.

The present invention is directed to a process of isolating and purifying a newly-identified staphylococcal enterotoxin designated SEH. SEH elicits an emetic response in monkeys, and is antigenically and serologically distinct from previously known SE's. The emetic activity of SEH is neutralized only by antibodies specific to it, and the emetic activity of SEH is unaffected by both antibodies specific to previously known SE's and antibodies specific to toxic shock syndrome toxin 1. Immunodiffusion assay shows the lack of cross-reactivity between SEH and previously known SE's. (See FIG. 6).

PRODUCTION AND PURIFICATION OF S. AUREUS ENTEROTOXIN H (SEH)

The present invention provides a simple, high-yield process for isolating and purifying novel SE's which employs ion-exchange and gel-permeation chromatographic techniques. The isolation and purification steps can be accomplished with relative ease and modest cost using commercially available materials.

The process provides ample SEH antigen for antibody production. This allows for the development of SEH detection protocols. Both polyclonal and monoclonal antibodies can be produced which are highly specific for SEH. For brevity and clarity, the following discussion will focus on the generation and use of polyclonal antibodies specific to SEH. This focus is for brevity only, and is not to limit the invention in any fashion. The present invention functions equally well with either monoclonal antibodies, polyclonal antibodies, or combinations thereof.

Polyclonal antibodies specific to SEH have been produced and used to develop reliable, specific, rapid, and commercially cost-effective immunoassays for SEH, a previously uncharacterized enterotoxin.

Growth Parameters and Bacterial Strains

Initially, a number of different of S. aureus strains were cultured which are known to produce unidentified SE's. While the majority of SE's are produced by strains of S. aureus, there is some evidence that SE's are produced by other staphylococcal species such as S. intermedius and S. hyicus (Bergdoll, 1989). Therefore, while the following discussion is limited to production of SEH by strains of S. aureus, the production, isolation, and purification protocols described herein are equally applicable to other microorganisms suspected of producing SE's.

Unidentified SE's including SEH were produced by cultivating the S. aureus strains shown in Tables 1 and 2 according to the sac culture method as described in Su and Wong, 1993. S. aureus strains were grown in 6% NZ Amine A plus 1% yeast extract, and incubated at 37° C. for 24 hours. The culture conditions were modified as described in Su and Wong, incorporated herein by reference, to maximize the production of unidentified SE's.

Table 1 is a list of the S. aureus strains cultured that are known to produce at least one previously-identified SE, and perhaps unidentified SE's. Table 2 is a list of the S. aureus strains cultured which have been reported to not produce any previously-identifiable SE (Kokan and Bergdoll, 1987).

As can be seen from Table 2, FRI-569 produces the largest amount of SEH of any of the strains tested (230 ng/mL), and is therefore the preferred S. aureus strain for production of crude SEH.

Harvest of Staphylococcal Enterotoxin

Enterotoxins (if any) produced by the various staphylococcal strains are harvested from the culture supernate. Cell bodies may be separated from the growth medium by any acceptable method, including filtration, precipitation, or centrifugation. Preferably, cell-free culture supernate is obtained by centrifuging the culture fluids at 20,000 33 g for 20 minutes.

Concentration and Purification of SEH

Concentration and purification of SEH is accomplished by adsorption of proteinaceous material from the culture supernate, followed by ion-exchange and gel filtration chromatography to separate the SE proteins from any remaining proteinaceous components.

The preferred protocol is as follows:

Starting with cell-free culture supernate fluids, the supernate is first subjected to adsorption chromatography using Amberlite CG-50 resin (Sigma Chemical Company, St. Louis, Mo.), or any functionally equivalent adsorption matrix. Adsorbed materials are eluted using an appropriate buffer solution. A phosphate buffer solution containing 0.5 M NaCl, pH 6.2, is preferred. The adsorption may be carried out at ambient temperatures. The entire eluate is concentrated by known methods, and optionally dialyzed overnight at 4° C. against 5 mM phosphate buffer, pH 5.6.

The concentrated eluate obtained by adsorption chromatography is then subjected to ion-exchange chromatography at ambient temperatures. The preferred ion-exchange resin is CM-Sepharose FL resin (Pharmacia Biotech, Inc., Piscataway, N.J.), or a functionally equivalent resin. Materials adsorbed to the resin are eluted using a buffered gradient of increasing basicity, preferably ranging from pH 6.0 to pH 6.8. Eluted fractions containing SE's are pooled, concentrated by known methods, and optionally dialyzed as described above. The concentrated eluate obtained by ion-exchange chromatography is then further purified by gel filtration chromatography. The preferred filtration medium is Sephacryl 100 HR gel (Pharmacia Biotech Inc., Piscataway, N.J.), or any functionally equivalent gel. Separation of the component proteins is preferably carried out at 4° C. using an eluent of 0.05M phosphate buffer solution containing 0.5 M NaCl, pH 6.8. Fractions containing SE's are pooled, concentrated by known methods, optionally dialyzed as described above, and lyophilized.

TABLE 1

SEH production by S. aureus strains producing one identified SE.

| S. aureus strains | SEH production (ng/ml)[1] |
|---|---|
| SEA producers: | |
| FRI-100 | —[2] |
| FRI-166 | — |

TABLE 1-continued

SEH production by *S. aureus* strains producing one identified SE.

| S. aureus strains | SEH production (ng/ml)[1] |
|---|---|
| FRI-196E | — |
| FRI-369 | — |
| SEB producers: | |
| FRI-376 | — |
| FRI-380 | — |
| FRI-748 | — |
| FRI-947 | — |
| SEC producers: | |
| FRI-137 | 142 |
| FRI-361 | — |
| FRI-429 | — |
| FRI-913 | — |
| SED producers: | |
| FRI-472 | — |
| FRI-776 | 52 |
| FRI-999 | — |
| FRI-1151M | 164 |
| SEE producers: | |
| FRI-326 | — |
| FRI-918 | — |
| FRI-919 | — |
| FRI-920 | — |

[1] Determined by ELISA with detection limit of 2.5 ng/ml.
[2] Not detectable.

TABLE 2

SEH production by *S. aureus* strains that did not produce any identified SE when grown by the membrane-over-agar method.

| S. aureus strains | SEH production (ng/ml)[1] |
|---|---|
| FRI-222 | —[2] |
| FRI-320 | — |
| FRI-388 | — |
| FRI-399 | 138 |
| FRI-411 | — |
| FRI-416 | — |
| FRI-431 | 18 |
| FRI-445 | 109 |
| FRI-450 | 52 |
| FRI-451 | — |
| FRI-453 | 144 |
| FRI-517 | — |
| FRI-527 | — |
| FRI-543 | 132 |
| FRI-553 | 42 |
| FRI-563 | 13 |
| FRI-569 | 230 |
| FRI-622 | — |
| FRI-772 | — |
| FRI-781 | 84 |
| FRI-857 | — |

[1] Determined by ELISA with detection limit of 2.5 ng/ml.
[2] Not detectable.

The lyophilized product from Sephacryl gel filtration is then redissolved in an elution buffer and again subjected to gel filtration chromatography. The preferred filtration medium here is Bio-Gel P-30 gel (Bio-Rad Laboratories, Hercules, Calif.), or any functional equivalent thereof. Separation of the component proteins is preferably carried out at 4° C. with a 0.05M phosphate buffer solution containing 0.5M NaCl, pH 6.8. Fractions containing SE's are pooled, concentrated by known methods, optionally dialyzed as described above, and lyophilized to yield a purified staphylococcal enterotoxin which is serologically and antigenically distinct from known SE's. This purified SE has been designated SEH.

Protein content of the various chromatographic eluates obtained in the above purification steps were monitored by ultraviolet absorption at 280 nm. Complete step-wise protein recovery from 2 liters of culture supernate fluids is shown in Table 3.

TABLE 3

Protein recovery during purification of SEH.

| Preparation | Total Protein[1] |
|---|---|
| Culture Supernatant (2L) | 19.8 g |
| SEH Positive Pool from: | |
| CG-50 | 578 mg |
| CM-Sepharose FL | 11.0 mg |
| Sephacryl 100 HR | 2.2 mg |
| Bio-Gel P-30 | 63 µg |

[1] Determined by the BCA protein assay from Pierce, Rockford, IL.

Another protocol to isolate and purify SEH is to pass cell-free culture supernate fluids over a strongly anionic ion-exchange resin. A preferred resin is Productiv (TM) QM (MetaChem Technologies, Inc., Torrance, Calif. Supernate fluids are adjusted to approximately pH 6.0, and passed through a Productiv QM cartridge. Adsorbed proteinaceous material is then eluted from the cartridge with an acetate buffer solution. Eluates containing SEH are then concentrated as described above.

The concentrated eluate from the above step is then passed over a weakly anionic ion-exchange resin to further purify the SEH. The concentrated eluate is again adjusted to approximately pH 6.0 and passed through an anion exchange column. A preferred resin is a Productiv (TM) DE cartridge. Adsorbed proteinaceous material is eluted from the cartridge using acetate buffer. The eluate is concentrated, dialyzed, and lyophilized as described above to yield substantially pure SEH.

If needed or desired, the lyophilized SEH can be dissolved in a buffer solution and subjected to gel filtration chromatography as described above.

Still another method to isolate substantially pure SEH is to subject the crude protein mixture obtained by batch adsorption or anionic exchange chromatography to affinity chromatography using antibodies specific to SEH as ligands. Several different matrix materials for affinity chromatography are commercially available.

Detection of Staphylococcal Enterotoxins

Detection of the presence of SE's after each purification step was accomplished using the standard monkey feeding assay described above. In short, chromatographic fractions of the peaks from each individual chromatographic step were pooled and given intragastrically to young rhesus monkeys (1–2 years old). In other words, eluates were tested after each chromatographic separation. If emesis was observed in monkeys within 5 hours after feeding, the fractions were considered to contain SE's.

A control group of monkeys was fed doses of the raw SE-containing culture supernate to which was added a mixed serum containing antiserum to each of the known SE's (SEA to SEE), as well as antiserum to toxic shock syndrome toxin 1 (TSST-1) (Reiser et al., 1983). The control group was constructed to exclude the possibility of emesis induction in monkeys by any of the already known SE's or by TSST-1. Results for the test and control groups are shown in Table 4.

TABLE 4

Monkey feeding assay of SEH.

| Materials fed | Antiserum used | Monkeys vomited/ Monkeys fed |
|---|---|---|
| Culture Supernatant[1] (50 ml) | None | 2/2 |
| Culture Supernatant (50 ml) | Heterologous[2] | 2/2 |
| Culture Supernatant (50 ml) | SEH | 0/2 |
| Purified SEH (30 μg) | None | 1/1 |
| Purified SEH (30 μg) | SEH | 0/1 |

[1]From the growth of *S. aureus* strain FRI-569 in 6% NA-Amine A plus 1% yeast extract by sac culture method (Su and Wong, 1993).
[2]Mixture of antisera to SEA, SEB, SEC, SED, SEE, and TSST-1.

Identification and Characterization of SEH

The molecular weight of SEH obtained by the above-described process was determined by two different conventional methods: Sodium dodecyl sulfate polyacrylamide gel electrophoresis (SDS-PAGE) (Laemmli, 1970, incorporated herein by reference), and gel filtration chromatography. Gel filtration was performed on Sephacryl 100 HR calibrated with a low-molecular weight calibration kit from Pharmacia. The molecular weight of SEH was found to be 28.5 kD (SDS-PAGE) (see FIG. 4), which compares favorably with the value of 27.3 kD as measured by gel filtration.

Isoelectric focusing of SEH revealed a single band located between the pI markers of 5.2 and 5.85. (See FIG. 5). The isoelectric point of SEH is estimated to be approximately 5.7.

After SDS-PAGE, the developed proteins were transferred (electro-blotted) to polyvinylidene difluoride (PVDF) membranes for N-terminal amino acid sequencing. The membranes were stained using conventional methods and the stained protein band sequenced by conventional methodology at the Protein/Nucleic Acid Shared Facility at the Medical College of Wisconsin using an Applied Biosystems pulsed liquid phase sequencer, model 477A. The N-terminal amino acid sequence of SEH was determined to be: Glu Asp Leu His Asp Lys Ser Glu Leu Thr Asp Leu Ala Leu Ala Asn Ala Tyr Gly Gln Tyr Asn His Pro Phe lie Lys Glu Asn Ile.

This N-terminal amino acid sequence is different from any of the previously-characterized SE's.

Immunodiffusion assay by the method of Robbins et al. 1974, incorporated herein by reference, shows no cross-reactivity between known SE's and SEH. See FIG. 6. Each previously identified SE, and TSST-1 formed precipitin lines only with its respective anti-serum. Anti-serum specific to the known SE's and TSST-1 did not react with SEH, and anti-serum specific to SEH (see below) reacted only with SEH.

Additionally, Western blot analysis of culture supernate from cultures of *S. aureus* strain FRI-572, a strain known to contain the seg+gene for SEG, shows that SEH is distinct from SEG, and that this *S. aureus* strain does not produce SEH. Culture supernate from the growth of *S. aureus* strain FRI-572 was subjected to SDS-PAGE, blotted to nitrocellulose paper, exposed to antibodies specific to SEH, and stained by known methodology, in parallel with pure SEH. The results are shown in FIG. 7.

BIOREAGENTS

Both the crude protein mixture and purified SEH can be employed as bioreagents. The crude proteins and purified SEH can be used to prepare polyclonal and monoclonal antibodies for the detection of SEH. The antibodies can be assembled into ready-to-use test kits for the rapid determination of SEH contamination.

PRODUCTION OF ANTIBODIES TO SEH

Antibodies, either polyclonal or monoclonal, can be prepared by any method known in the art. Monoclonal antibodies can be produced by any known method, for example, the method described by Fazekus et al. (1980). Polyclonal antibodies to both crude SEH from CG-50 batch adsorption, and purified SEH, were produced in adult New Zealand white rabbits at the Animal Care Unit of the University of Wisconsin-Madison Medical School. (See Robbins et al., 1984) An illustrative methodology to produce polyclonal antibodies using the crude SEH is as follows:

A total of 500 μg crude SEH is emulsified with complete Freund's adjuvant (CFA) and intradermally injected into rabbits at multiple sites. Four week later, the rabbits receive a subcutaneous booster injection of 1 mg of crude SEH emulsified with incomplete Freund's adjuvant (ICFA). Blood is collected two weeks after the booster is administered. Serum is collected by centrifugation at 5900 ×g for 20 minutes.

Antibody to pure SEH can be prepared by multiple-site intradermal injection of 3 μg of SEH emulsified with CFA. Booster injections of 12, 50, and 100 μg of SEH emulsified with ICFA is given subcutaneously at weeks 4, 8, and 11, respectively. Blood and serum are then obtained as described immediately above.

DOUBLE-ANTIBODY SANDWICH ENZYME-LINKED IMMUNOSORBENT ASSAY FOR THE DETECTION OF SEH

Using the anti-SEH antibodies obtained above, a non-competitive double-antibody sandwich enzyme-linked immunosorbent assay (ELISA) for the detection of SEH was constructed. ELISA's are a sensitive and reliable method for assaying the presence of a given antigen within a sample.

In general, ELISA's operate by conjugating an antibody specific to the antigen to be assayed to a label, normally an enzyme. The antibody is cultured on a multi-well plate. The sample to be tested is then introduced into one series of wells and incubated. A parallel series of wells is cultured with solutions containing known concentrations of the antigen to be assayed. The antibody-enzyme conjugate is then introduced into the wells. The affinity of the antibody-enzyme conjugate for the antigen will cause binding between the two. Lastly, a labelled substrate which binds to the enzyme of the antibody-enzyme conjugate is added to all of the wells. The substrate generates a measurable response (color, etc.) which is proportional to the amount of binding between the antibody-enzyme conjugate and the antigen to be assayed. A curve constructed from the standard cultures is then used to determine the amount of antigen present in the samples tested. (Saunders et al., 1977; Saunders, 1979).

Here, antibody-enzyme conjugate is prepared by coupling peroxidase to SEH antibodies. Antibody-enzyme conjugate is separated from unconjugated antibody and free peroxidase by Sephacryl 300 gel filtration chromatography. FIG. 8 shows an elution profile of such a separation (antibody-enzyme conjugate eluted in peak A). Fractions containing the conjugate are pooled, concentrated by known methods, dialyzed against phosphate buffer as described above, mixed with a stabilizing solution, and lyophilized.

First, anti-SEH antibodies are dissolved in carbonate buffer, plated onto a 96-well, non-sterile polystyrene plate, and incubated overnight.

To construct a standard absorption curve, SEH solutions of known concentrations are then introduced into a first series of wells. An SEH free solution is also incubated into a series of wells for a negative control. The standard ELISA curve shown in FIG. 9 was constructed using SEH solutions having concentrations of 1.3, 2.5, 5, 10, 25, 50, 100, and 200 ng/mL SEH, with Absorbance measured at 410 nm.

Culture supernate fluids from the growth of *S. aureus* strains are first pre-incubated with rabbit serum to prevent non-specific reactions caused by protein A (Freed et al, 1982), and then added to a series of wells. The wells are then washed to remove unbound SEH. Antibody-enzyme conjugate is introduced into the wells, and the wells are again washed to remove uncomplexed conjugate.

A labelled substrate is then added to the wells, and the plate allowed to develop. After a suitable period of time, color development in the wells is stopped by addition of a stopping solution (EDTA). The absorbance of each culture is then taken, using well-known methodologies.

The amounts of SEH in a sample are then determined by converting the net absorption value for a given sample to the corresponding concentrations via the standard curve.

Using the ELISA described above, SEH can be reliably detected in amounts as small as approximately 2.5 ng/ml.

Supernates from various *S. aureus* strains were tested with the ELISA of the present invention. It was found that three of twenty strains of *S. aureus* that produce at least one of the known SE's also produce SEH.

The ELISA was also used to show that ten of twenty-one strains of *S. aureus* which are known to produce unidentified SE's as shown by the monkey feeding assay gave positive results for the presence of SEH. Since eleven of these strains are known to produce SE's, but did not test positive using the present ELISA, it must be concluded that other serological types of SE's exist.

EXAMPLE

The following Example is provided to illustrate the advantages of the present invention and to assist one of ordinary skill in the art in making and using the same. The Example is for illustrative purposes only, and is not intended to limit the scope of the claimed invention in any manner.

Cultivation of *Staphylococcus aureus*

*S. aureus* strain FRI-569 was obtained from the culture collection at the Food Research Institute of the University of Wisconsin, Madison, Wis., and cultured as described above.

Step I - Amberlite CG-50 Batch Adsorption

Two liters of culture supernate fluids, pH 8.1–8.6, collected from the growth of *S. aureus* strain FRI-569 were adjusted to pH 5.6 with 6N HCl and diluted five-fold to 10 L with distilled water. Amberlite CG-50 resin (400 mL, wet volume), pre-cycled with 6N NaOH followed by 6N HCl and equilibrated with 5 mM phosphate buffer, pH 5.6, was added to the diluted supernate fluid and stirred for two hours at ambient temperature. After mixing, the resin was allowed to settle and the supernate fluid removed.

The resin was packed into a column to a bed height of 86 cm and washed with 2.5 L of 5 mM phosphate buffer, pH 5.6. The adsorbed materials were eluted with 5 L of 0.5M phosphate buffer containing 0.5M NaCl, pH 6.2, at a flow rate of 150 mL/h. The entire eluate was concentrated to 500 mL by a Pellicon cassette system (Millipore, Bedford, Mass.) with a 10,000 nominal molecular weight limit cassette. The eluate was further concentrated to 60 mL by a stirred cell (Amicon, Beverley, Mass.) with a PM10 membrane (10,000 molecular weight cutoff). The concentrated eluate was dialyzed against 5 mM phosphate buffer, pH 5.6, overnight at 4° C.

Step II - CM-Sepharose FL Ion-Exchange Chromatography

The dialyzed eluate from CG-50 adsorption was clarified by centrifugation and applied at a flow rate of 40 mL/h to a chromatographic column containing 150 mL (wet volume) of CM-Sepharose FL, bed height 28 cm. The column was washed with 400 mL of 5 mM phosphate buffer, pH 5.06, at a flow rate of 60 mL/h. The adsorbed materials were eluted at a flow rate of 60 mL/h with 1 L of each of the following three phosphate buffers: 0.03M, pH 6.0; 0.045M, pH 6.4; and 0.06M, pH 6.8. 300 mL of 0.5M phosphate buffer containing 0.5M NaCl, pH 6.8, was used to remove all of the remaining materials bound to the gel. Fractions containing SEH were pooled, concentrated to 5 mL, and dialyzed as described above.

Step III- Sephacryl 100 HR Gel Filtration

Concentrated SEH was applied to a chromatographic column containing 500 mL of Sephacryl 100 HR, bed height 92 cm. The column was eluted with 0.05M phosphate buffer containing 0.5M NaCl, pH 6.8, at a flow rate of 50 mL/h. Fractions containing SEH were pooled, concentrated, dialyzed as described above, and lyophilized.

Step IV Bio-Gel P-30 Gel Filtration

One half of the lyophilized toxin from Sephacryl 100 HR gel filtration was dissolved in 1 mL of elution buffer, and applied to a chromatographic column packed with 500 mL of Bio-Gel P-30 gel (Bio-Rad Laboratories, Hercules, Calif.), and separated with 0.05M phosphate buffer containing 0.5M NaCl, pH 6.8, at a flow rate of 15 mL/h. Fractions containing SEH were pooled, concentrated, dialyzed, and lyophilized as described above. The second half of the lyophilized toxin from Sephacryl 100 HR was processed in an identical fashion.

The product protein was then subjected to SDS-PAGE, isoelectric focusing, Western blot analysis, and N-amino acid sequencing as described above.

To determine whether SEH was present during the stepwise purification process, initially a monkey feeding assay was performed after each separation step, as described above. After all of the process steps were determined, complete isolation and purification of SEH was carried out, omitting the intermediate monkey feeding assays.

The SEH purified using the above-described process yielded only one band on SDS-PAGE under both reducing and non-reducing conditions. (See FIG. 4.) The experimental results indicate that similar to previously-identified SE's, SEH appears to be a simple, emetic, and antigenic protein.

It is understood that the present invention is not limited to the particular reagents, steps, or methods disclosed herein, but rather embraces all such forms thereof as come within the scope of the attached claims.

SEQUENCE LISTING ( 1 ) GENERAL INFORMATION:

( i i i ) NUMBER OF SEQUENCES: 1

(2) INFORMATION FOR SEQ ID NO:1:

(i) SEQUENCE CHARACTERISTICS:
        (A) LENGTH: 30 amino acids
        (B) TYPE: amino acid
        (C) STRANDEDNESS: unknown
        (D) TOPOLOGY: unknown     (ii) MOLECULE TYPE: peptide     (v) FRAGMENT TYPE: N-terminal     (vi) ORIGINAL SOURCE:
        (A) ORGANISM: Staphylococcus aureus     (xi) SEQUENCE DESCRIPTION: SEQ ID NO:1:

```
Glu Asp Leu His Asp Lys Ser Glu Leu Thr Asp Leu Ala Leu Ala Asn
 1               5                  10                  15

Ala Tyr Gly Gln Tyr Asn His Pro Phe Ile Lys Glu Asn Ile
            20                  25                  30
```

BIBLIOGRAPHY

Avena, R. M. and M. S. Bergdoll. 1967. Purification and some physicochemical properties of enterotoxin C, *Staphylococcus aureus* strain 361. Biochemistry. 6:1474–1480.

Bergdoll, M. S., M. J. Surgalla, and G. M. Dack. 1959. Staphylococcal enterotoxin: identification of a specific precipitating antibody with enterotoxin neutralizing property. J. Immunol. 83:334–338.

Bergdoll, M. S., C. R. Borja, and R. M. Avena. 1965. Identification of a new enterotoxin as enterotoxin C. J. Bacteriol. 90:1481–1485.

Bergdoll, M. S., C. R. Borja, R. N. Robbins, and K. F. Weiss. 1971. Identification of enterotoxin E. Infect. Immun. 4:593–595.

Bergdoll, M. S. 1983. Enterotoxins, p. 559–598. In C. Adlam and C. S. F. Easmon (ed.), Staphylococci and Staphylococcal Infections, Vol. 2. Academic Press, Inc., London.

Bergdoll, M. S. 1989. *Staphylococcus aureus*, p. 463–523. In M. P. Doyle (ed.), Foodborne Bacterial Pathogens. Marcel Dekker, Inc., New York.

Betley, M. J., D. W. Borst, and L. B. Regassa. 1992. Staphylococcal enterotoxins, toxic shock syndrome toxin and streptococcal pyrogenic exotoxins: a comparative study of their molecular biology. Chem. Immunol. 55:1–35.

Casman, E. P. 1960. Further serological studies of staphylococcal enterotoxin. J. Bacteriol. 79: 849–856.

Casman, E. P., R. W. Bennett, A. E. Dorsey, and J. A. Issa. 1967. Identification of a fourth staphylococcal enterotoxin, enterotoxin D. J. Bacteriol. 94:1875–1882.

Fazekus et al., 1980. J. Immunol. Methods, 35:1.

Freed, R. C., M. L. Evenson, R. F. Reiser, and M.S. Bergdoll. 1982. Enzyme-linked immunosorbent assay for detection of staphylococcal enterotoxins in food. Appl. Environ. Microbiol. 44: 1349–1355.

Kokan, N. P. and M. S. Bergdoll. 1987. Detection of low-enterotoxin-producing *Staphylococcus aureus* strains. Appl. Environ. Microbiol. 53:2675–2676.

Laemmli, U. K. 1970. Cleavage of structural proteins during the assembly of the head of bacteriophage T4. Nature. 227:680–685.

Munson, S. H. and M. J. Betley. 1991. Partial characterization of a new staphylococcal enterotoxin gene, abstr. B-36, p. 31. Abstr. 91th Annu. Meet. Am. Soc. Microbiol. 1991.

Reiser, R. F., R. N. Robbins, G. P. Khoe, and M. S. Bergdoll. 1983. Purification and some physicochemical properties of toxic-shock toxin. Biochem. 22:3907–3912.

Reiser, R. F., R. N. Robbins, A. L. Noleto, G. P. Khoe, and M. S. Bergdoll. 1984. Identification, purification, and some physicochemical properties of staphylococcal enterotoxin $C_3$. Infect. Immun. 45:625–630.

Robbins, R. N., and M.S. Bergdoll. 1984. Production of rabbit antisera to the staphylococcal enterotoxins. J. Food Prot. 47:172–176.

Robbins, R., S. Gould, and M. Bergdoll. 1974. Detecting the enterotoxigenicity of *Staphylococcus aureus* strains. Appl. Microbiol. 28:946–950.

Saunders, G. C. 1979. The art of solid enzyme immunoassay including selected protocols, pp. 98–119. In R. M. Nakamura, R. W. Dito, and E. S. Tucker (ed.), Immunoassays in the clinical laboratory. Alan R. Liss, Inc., New York.

Saunders, G. C., and M. L. Bartlett. 1977. Double-antibody solid-phase enzyme immunoassay for the detection of staphylococcal enterotoxin A. Appl. Environ. Microbiol. 34:518–522.

Su, Y.-C. and A. C. L. Wong. 1993. Optimal condition for the production of unidentified staphylococcal enterotoxins. J. Food Prot. 56:313–316.

Surgalla, M. J., M. S. Bergdoll, and G. M. Dack. 1953. Some observations on the assay of staphylococcal enterotoxin by the monkey-feeding test. J. Lab. Clin. Med. 41:782–788.

Todd, E. C. D. 1989. Preliminary estimates of costs of foodborne disease in the United States. 1989J. Food Prot. 52:595–601.

What is claimed is:

1. A generally pure protein composition isolated from staphylococci containing a protein having an N-terminal amino acid sequence of Glu Asp Leu His Asp Lys Ser Glu Leu Thr Asp Leu Ala Leu Ala Asn Ala Tyr Gly Gln Tyr Asn His Pro Phe Ile Lys Glu Asn Ile, SEQ. ID. NO. 1, and having the following characteristics:

| Isoelectric point | 5.7 | |
|---|---|---|
| Molecular weight | 28.5 kD | (SDS-PAGE) |
| | 27.3 kD | (gel filtration). |

2. The generally pure protein composition of claim 1, wherein said substantially pure protein is isolated from *Staphylococcus aureus*.

3. A generally pure staphylococcal enterotoxin designated SEH having an N-terminal amino acid sequence of Glu Asp Leu His Asp Lys Ser Glu Leu Thr Asp Leu Ala Leu Ala Asn Ala Tyr Gly Gln Tyr Asn His Pro Phe Ile Lys Glu Asn Ile, SEQ. ID. NO. 1, and having the following characteristics:

| Isoelectric point | 5.7 | |
|---|---|---|
| Molecular weight | 28.5 kD | (SDS-PAGE) |
| | 27.3 kD | (gel filtration). |

4. The generally pure staphylococcal enterotoxin SEH of claim 3, wherein said SEH is isolated from *Staphylococcus aureus*.

5. A bioreagent comprising a substantially pure protein composition containing a protein having an N-terminal amino acid sequence of Glu Asp Leu His Asp Lys Ser Glu Leu Thr Asp Leu Ala Leu Ala Asn Ala Tyr Gly Gln Tyr Asn His Pro Phe Ile Lys Glu Asn Ile, SEQ. ID. NO. 1, and having the following characteristics:

| Isoelectric point | 5.7 | |
|---|---|---|
| Molecular weight | 28.5 kD | (SDS-PAGE) |
| | 27.3 kD | (gel filtration). |

6. A protein composition isolated from staphylococci containing a protein having an N-terminal amino acid sequence, of Glu Asp Leu His Asp Lys Ser Glu Leu Thr Asp Leu Ala Lea Ala Asn Ala Tyr Gly Gln Tyr Asn His Pro Phe Ile Lys Glu Asn Ile, SEQ. ID. NO. 1.

7. The protein composition of claim 6, wherein said substantially pure protein composition is isolated from *Staphylococcus aureus*.

8. A staphylococcal enterotoxin designated SEH having an N-terminal amino acid sequence of Glu Asp Leu His Asp Lys Ser Glu Leu Thr Asp Leu Ala Leu Ala Asn Ala Tyr Gly Gln Tyr Asn His Pro Phe Ile Lys Glu Asn Ile, SEQ. ID. NO. 1.

9. The staphylococcal enterotoxin SEH of claim 8, wherein said SEH is isolated from *Staphylococcus aureus*.

10. A bioreagent comprising a protein composition containing a protein having an N-terminal amino acid sequence of Glu Asp Leu His Asp Lys Ser Glu Leu Thr Asp Leu Ala Leu Ala Asn Ala Tyr Gly Gln Tyr Asn His Pro Phe Ile Lys Glu Asn Ile, SEQ. ID. NO. 1.

* * * * *

UNITED STATES PATENT AND TRADEMARK OFFICE
CERTIFICATE OF CORRECTION

PATENT NO. : 5,601,830
DATED : February 11, 1997
INVENTOR(S) : Yi C. Su; Amy C. Lee Wong It is certified that error appears in the above-identified patent and that said Letters Patent is hereby corrected as shown below:

IN THE CLAIMS

Column 16, Line 4: Delete "Lea" and substitute -- Leu -- therefor.

Signed and Sealed this

Fourteenth Day of April, 1998

Attest:

BRUCE LEHMAN

Attesting Officer                Commissioner of Patents and Trademarks